(12) United States Patent
Akiyama

(10) Patent No.: US 9,056,034 B2
(45) Date of Patent: Jun. 16, 2015

(54) ABSORBENT PRODUCT

(75) Inventor: Ikuo Akiyama, Mima-gun (JP)

(73) Assignee: LIVEDO CORPORATION, Ehime (JP)

( * ) Notice: Subject to any disclaimer, the term of this patent is extended or adjusted under 35 U.S.C. 154(b) by 559 days.

(21) Appl. No.: 13/203,089

(22) PCT Filed: Nov. 15, 2010

(86) PCT No.: PCT/JP2010/006703
§ 371 (c)(1),
(2), (4) Date: Aug. 24, 2011

(87) PCT Pub. No.: WO2011/070728
PCT Pub. Date: Jun. 16, 2011

(65) Prior Publication Data
US 2011/0313384 A1    Dec. 22, 2011

(30) Foreign Application Priority Data

Dec. 10, 2009  (JP) .................................. 2009-280100

(51) Int. Cl.
*A61F 13/15*      (2006.01)
*A61F 13/535*     (2006.01)
*A61F 13/494*     (2006.01)
(Continued)

(52) U.S. Cl.
CPC ............. *A61F 13/535* (2013.01); *A61F 13/534* (2013.01); *A61F 13/536* (2013.01); *A61F 13/49473* (2013.01); *A61F 13/5323* (2013.01); *A61F 13/53717* (2013.01); *A61F 13/53747* (2013.01)

(58) Field of Classification Search
USPC ................... 604/378, 385.101, 379, 382, 383, 604/385.01, 368
See application file for complete search history.

(56) References Cited

U.S. PATENT DOCUMENTS

| 4,988,344 A | 1/1991 | Reising et al. |
| 5,411,497 A | 5/1995 | Tanzer et al. |

(Continued)

FOREIGN PATENT DOCUMENTS

| CN | 1819811 | 8/2006 |
| CN | 1913854 | 2/2007 |

(Continued)

OTHER PUBLICATIONS

International Search Report issued Mar. 22, 2011 in International (PCT) Application No. PCT/JP2010/006703.

*Primary Examiner* — Jacqueline Stephens
(74) *Attorney, Agent, or Firm* — Wenderoth, Lind & Ponack, L.L.P.

(57) ABSTRACT

In an absorbent part of an absorbent product, super absorbent materials located between two sheets in an absorbent area swell by absorption of moisture of excrement, and spaces extending in a longitudinal direction from an opening, which is formed at a portion of upper absorbent layer facing the crotch region of a wearer, are formed between a non-absorbent area where the super absorbent materials do not exist and the upper absorbent layer and between the non-absorbent area and a lower absorbent layer. In the absorbent product, through the spaces, moisture of excrement in the second excretion and later can be quickly diffused over a wide area along the longitudinal direction of the absorbent part, and the moisture of excrement can be absorbed in a wide area of the absorbent part. As a result, it is possible to maintain high absorbing ability in multiple excretions in the absorbent product.

14 Claims, 9 Drawing Sheets

(51) Int. Cl.
*A61F 13/532* (2006.01)
*A61F 13/537* (2006.01)
A61F 13/534 (2006.01)
A61F 13/536 (2006.01)

(56) References Cited

U.S. PATENT DOCUMENTS

| | | | |
|---|---|---|---|
| 5,425,725 A | 6/1995 | Tanzer et al. | |
| 5,433,715 A | 7/1995 | Tanzer et al. | |
| 5,593,399 A | 1/1997 | Tanzer et al. | |
| 5,713,881 A * | 2/1998 | Rezai et al. | 604/368 |
| 2006/0278335 A1 | 12/2006 | Moriura et al. | |
| 2007/0142802 A1 | 6/2007 | Suzuki | |
| 2008/0319408 A1 | 12/2008 | Uchimoto et al. | |

FOREIGN PATENT DOCUMENTS

| | | |
|---|---|---|
| CN | 101327156 | 12/2008 |
| EP | 0 343 941 | 11/1989 |
| EP | 2 055 280 | 5/2009 |
| JP | 2-60646 | 3/1990 |
| JP | 5-86320 | 11/1993 |
| JP | 8-191857 | 7/1996 |
| JP | 9-504206 | 4/1997 |
| JP | 9-504207 | 4/1997 |
| JP | 9-504208 | 4/1997 |
| JP | 9-504210 | 4/1997 |
| JP | 2005-185616 | 7/2005 |
| JP | 2005-253851 | 9/2005 |
| JP | 2009-327 | 1/2009 |
| JP | 2009-61230 | 3/2009 |
| KR | 10-0336052 | 10/2002 |

* cited by examiner

ABSORBENT PRODUCT

TECHNICAL FIELD

The present invention relates to an absorbent product for receiving excrement from a wearer.

BACKGROUND ART

A product where an absorbent part formed of crushed pulp and the like is provided between a top sheet and a back sheet, is conventionally used as an absorbent product such as a disposable diaper or an auxiliary absorbent pad. In Published Japanese Translation No. 9-504206 of PCT International Application No. PCT/US94/11707 (Document 1), Published Japanese Translation No. 9-504207 of PCT International Application No. PCT/US94/11708 (Document 2), Published Japanese Translation No. 9-504208 of PCT International Application No. PCT/US94/11709 (Document 3) and Published Japanese Translation No. 9-504210 of PCT International Application No. PCT/US94/11752 (Document 4), laminated structure of a fiber assembly layer of pulp or the like and an absorbent sheet where super absorbent materials are located in a plurality of pocket regions provided between two carrier layers, is proposed as an absorbent part of a disposable diaper.

Japanese Patent Application Laid-Open No. 8-191857 (Document 5) discloses an absorbent part where an upper core having an opening is laminated on a lower core through a hydrophilic nonwoven fabric. In a disposable diaper of Document 5, moisture of excrement toward an upper surface of the upper core is absorbed thereat, moisture which has passed through the opening of the upper core is received by the hydrophilic nonwoven fabric to be diffused, and therefore it is absorbed at boundary surfaces between the upper core and the lower core. In Japanese Patent Application Laid-Open No. 2005-185616 (Document 6), a disposable absorbent product where a diffusion layer is provided at a space within an opening of an upper core is proposed.

In a super absorbent material such as SAP (Super Absorbent Polymer) used for a disposable diaper or the like, moisture is slowly absorbed as compared to a fiber assembly layer of pulp or the like. Thus, in the case where an absorbent sheet having super absorbent materials is located on the fiber assembly layer of pulp or the like as shown in the disposable diapers of Documents 1 to 4, before moisture of excrement is absorbed into the absorbent sheet, the moisture possibly spreads widely to reach to the skin of the wearer or to leak out to the outer side of the disposable diaper.

In the disposable diapers of Documents 5 and 6, since the lower core is the fiber assembly layer of pulp or the like having relatively high absorption speed, moisture of excrement which has passed through the opening of the upper core is absorbed into the lower core before it is diffused widely by the hydrophilic nonwoven fabric. Thus, the moisture of excrement is mainly absorbed into portions of the upper and lower cores positioned in the vicinity of the opening, and whole the upper and lower cores can not be utilized efficiently to absorb moisture. Consequently, if after excretion, excretion is performed again without changing the disposable diaper, some moisture of excrement is not possibly absorbed and flows back through the opening, to reach over a wide area of the skin of the wearer or to leak out to the outer side of the disposable diaper. In addition, by the first excretion, the portions of the upper and lower cores positioned in the vicinity of the opening are swollen by absorption of moisture and the portions come into contact with each other with no space between them, and therefore the moisture of excrement which has passed through the opening is more poorly diffused in the second excretion and later.

SUMMARY OF INVENTION

The present invention is intended for an absorbent product for receiving excrement from a wearer. It is an object of the present invention to maintain high absorbing ability in multiple excretions in the absorbent product.

The absorbent product according to the present invention comprises: a liquid-pervious top sheet; a water-repellent or liquid-impervious back sheet; and an absorbent part located between the top sheet and the back sheet, wherein the absorbent part comprises: an upper absorbent layer having a fiber assembly layer in which an opening is formed at a position facing a crotch region of a wearer; and an absorbent sheet which is located between the upper absorbent layer and the back sheet and which covers the opening at the lower side of the opening, the absorbent sheet comprises: two sheets; and super absorbent materials which are located between the two sheets and which are fixed to at least one of the two sheets, and a low density area lies between the two sheets and spreads continuously from positions under the opening along a longitudinal direction of the absorbent part in the form of lines or mesh, and a density of the super absorbent materials in the low density area is lower than that in the other area of the absorbent sheet or the super absorbent materials do not exist in the low density area. In the present invention, it is possible to maintain high absorbing ability in multiple excretions.

According to an aspect of the present invention, the super absorbent materials do not exist in the low density area and the two sheets are bonded to each other in the low density area. It is therefore possible to diffuse moisture of excrement over a wider area between the upper absorbent layer and the absorbent sheet. Preferably, the two sheets are bonded to each other by heat bonding.

According to another aspect of the present invention, the low density area is in the form of mesh. According to still another aspect of the present invention, one of the two sheets which is located between the upper absorbent layer and the super absorbent materials is hydrophilic. In these cases, it is possible to diffuse moisture of excrement over a wider area between the upper absorbent layer and the absorbent sheet.

According to a preferred embodiment of the present invention, since the upper absorbent layer comprises a convex part protruding toward the top sheet and lying along an edge of the opening, it can be suppressed that excrement excreted into the opening flows out of the opening and spreads on the top sheet.

According to another preferred embodiment of the present invention, since the absorbent part further comprises a lower absorbent layer having a fiber assembly layer which is located between the absorbent sheet and the back sheet, absorption capacity in the absorbent part can be increased.

These and other objects, features, aspects and advantages of the present invention will become more apparent from the following detailed description of the present invention when taken in conjunction with the accompanying drawings.

DESCRIPTION OF EMBODIMENTS

Figure 1:
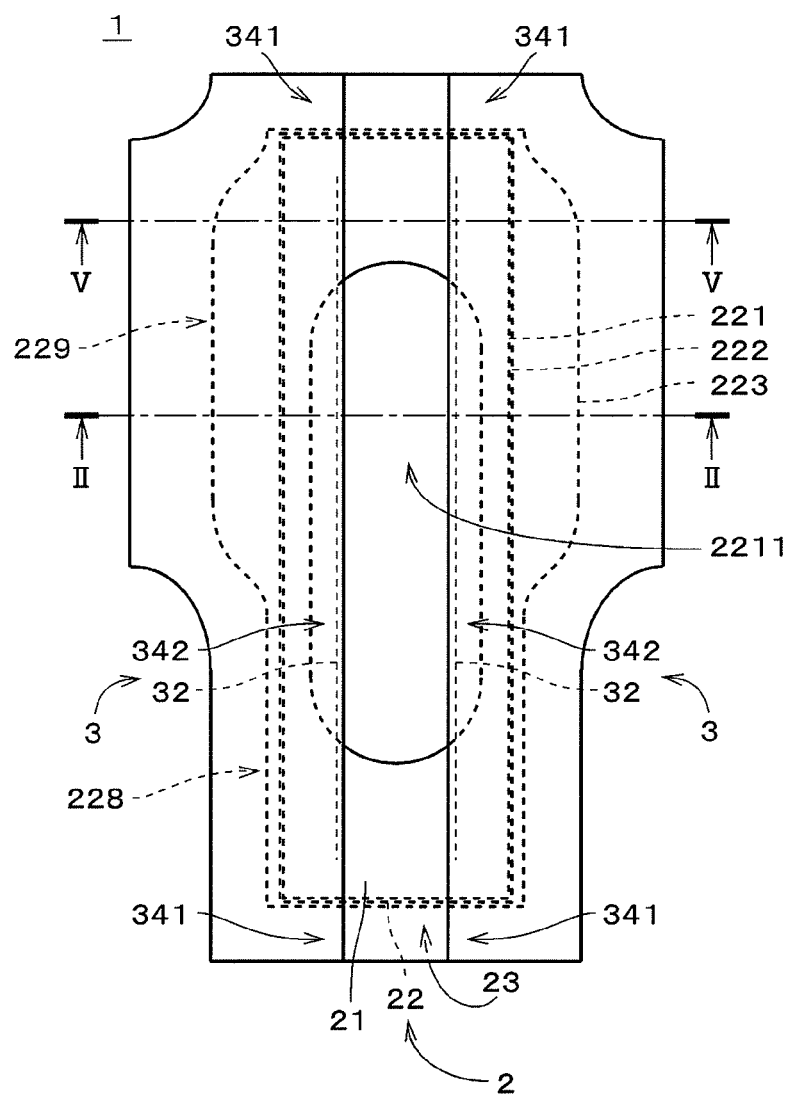
FIG. 1 is a plan view of an absorbent product in accordance with a first preferred embodiment.

FIG. 1 is a plan view of an absorbent product 1 in accordance with a first preferred embodiment of the present invention, and in FIG. 1 the absorbent product 1 is developed in a longitudinal direction. The absorbent product 1 is an auxiliary absorbent pad attached at the inside of a disposable diaper or the like which is an exterior product worn by a wearer, and it receives excrement from the wearer. FIG. 1 shows a surface of the absorbent product 1, which is to come into contact with the wearer's body during use, and hereinafter the surface is referred to as an "upper surface".

Figure 2:
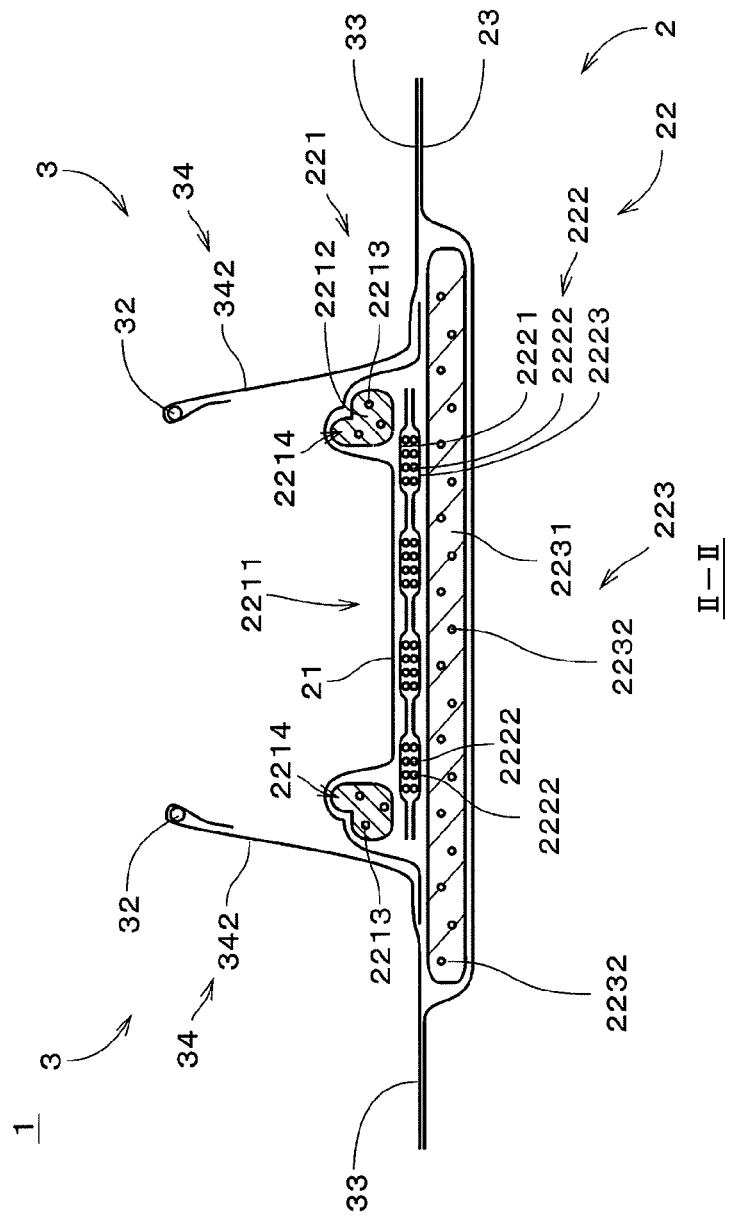
FIG. 2 is a cross-sectional view of the absorbent product.

FIG. 2 is a cross-sectional view of the absorbent product 1 taken along a line II-II in FIG. 1 where the absorbent product 1 is cross-sectioned with a plane orthogonal to the longitudinal direction (i.e., an up-down direction in FIG. 1). As shown in FIGS. 1 and 2, the absorbent product 1 has a sheet-like main body part 2 and a pair of side sheets 3 which is located on both side portions of the main body part 2 (i.e., the side portions are the left and right sides in FIGS. 1 and 2) and which extends across almost the entire length of the main body part 2 in the longitudinal direction. In FIG. 2, respective constituents of the absorbent product 1 are drawn so as to be slightly apart from one another for easy understanding of the drawing.

As shown in FIGS. 1 and 2, the main body part 2 has an absorbent part 22, a liquid-pervious top sheet 21 covering an upper surface (i.e., the surface of the wearer's side) of the absorbent part 22 which is one surface of the absorbent part 22, and a water-repellent or liquid-impervious back sheet 23 covering a lower surface of the absorbent part 22 which is the other surface of the absorbent part 22. Both left and right side portions of the top sheet 21 are bonded to the pair of side sheets 3 with hot melt adhesive, and the pair of side sheets 3 is bonded to the back sheet 23 at both left and right outer sides of the absorbent part 22 with hot melt adhesive. At both outer sides of the absorbent part 22 in the longitudinal direction, the top sheet 21 and the pair of side sheets 3 are bonded to the back sheet 23 with hot melt adhesive. The contours of constituent members of the absorbent part 22 located between the top sheet 21 and the back sheet 23 are drawn by thick broken lines in FIG. 1 for easy understanding of the drawing.

In the present embodiment, with respect to a width direction (i.e., a left-right direction in FIG. 1), a width of a portion 228 of the absorbent part 22 which is located on the downside of FIG. 1 is smaller than that of a portion 229 which is located on the upside of FIG. 1. In the following description, the portion 228 of the absorbent part 22 is referred to as the "narrow width part 228" and the portion 229 is referred to as the "wide width part 229". A width of an upper end of the wide width part 229 in FIG. 1 is smaller than the maximum width of the wide width part 229. In the case where the absorbent product 1 is used for a male, the absorbent product 1 is attached at the inside of a disposable diaper or the like so that the wide width part 229 is to be positioned on the front side (stomach side) of the wearer and the narrow width part 228 is to be positioned on the back side of the wearer. In the case where the absorbent product 1 is used for a female, the absorbent product 1 is attached at the inside of a disposable diaper or the like so that the narrow width part 228 is to be positioned on the front side of the wearer and the wide width part 229 is to be positioned on the back side of the wearer contrary to the male's case.

As shown in FIG. 2, an outside portion 33 of each side sheet 3 in the width direction (i.e., the outside portion is a side portion away from the other side sheet 3) is bonded on a portion of the top sheet 21 in the vicinity of its side edge in the width direction and bonded on portions of the absorbent part 22 and the back sheet 23 which are not covered with the top sheet 21, with hot melt adhesive, and the portion 33 lies across the entire length of the side sheet 3 in the longitudinal direction. In the following description, the outside portion 33 of each side sheet 3 is referred to as the "bonded part 33", and a portion 34 which lies on the inside of the bonded part 33 in the width direction and which is continuous with the bonded part 33 is referred to as the "side wall part 34". Bonding of the side sheet 3 to the top sheet 21, the back sheet 23 and the others may be performed by heat bonding, ultrasonic bonding or the like.

The side wall parts 34 are located on both side portions of the main body part 2, respectively, and extend across almost its entire length in the longitudinal direction. As shown in FIG. 1, side wall end parts 341 of each side wall part 34 which are both ends in the longitudinal direction are bonded on the main body part 2 with hot melt adhesive (or by heat bonding or ultrasonic bonding). In a standing part 342 between the two side wall end parts 341, an elastic member 32 extending in the longitudinal direction is bonded to the vicinity of an inside edge of the standing part 342 (i.e., the vicinity of a free edge) with hot melt adhesive. By contraction of the elastic member 32, the standing part 342 stands up toward the wearer as shown in FIG. 2, to become standing gathers which contact with the vicinity of wearer's groin.

The side sheet 3 is formed by folding a water-repellent or liquid-impervious nonwoven fabric (for example, a spunbond nonwoven fabric, meltblown nonwoven fabric or SMS (spunbond-meltblown-spunbond) nonwoven fabric), which is made of hydrophobic fibers (e.g., polypropylene, polyethylene, polyester, polyamide or nylon), into two portions at a folding line extending in the longitudinal direction, and by locating (sandwiching in) the elastic member 32 between the two portions overlapped with each other. For example, a polyurethane yarn, strip-like polyurethane film, yarn-like or strip-like natural rubber, or the like is used as the elastic member 32. In the present embodiment, a polyurethane yarn is used as the elastic member 32.

The top sheet 21 of the main body part 2 is a liquid-pervious sheet material, for example a nonwoven fabric made of hydrophilic fibers, and the top sheet 21 immediately catches moisture of excrement from the wearer and moves the moisture into the absorbent part 22. Examples of nonwoven fabrics used as the top sheet 21 are a point-bond nonwoven fabric, air-through nonwoven fabric, spunlace nonwoven fabric and spunbond nonwoven fabric, and as hydrophilic fibers for making these nonwoven fabrics, normally, cellulose, rayon, cotton and the like are used. As the top sheet 21, a liquid-pervious nonwoven fabric made of hydrophobic fibers (for example, polypropylene, polyethylene, polyester, polyamide or nylon) where hydrophilic treatment is performed on its surface with a surfactant or a porous plastic film may be utilized. In the present embodiment, an air-through nonwoven fabric whose weight per unit area is equal to or more than 10 $g/m^2$ and equal to or less than 35 $g/m^2$ is used as the top sheet 21.

As the back sheet 23, a water-repellent or liquid-impervious nonwoven fabric, a water-repellent or liquid-impervious plastic film, or a laminated sheet of the nonwoven fabric and the plastic film is used. The back sheet 23 prevents moisture of excrement or the like which has come to the back sheet 23, from leaking out to them outer side of the main body part 2. A spunbond nonwoven fabric, meltblown nonwoven fabric and SMS nonwoven fabric which are made of hydrophobic fibers, are exemplified as a nonwoven fabric used for the back sheet 23, and water-repellent treatment is performed on the nonwoven fabric as appropriate. In a case where a plastic film is used for the back sheet 23, it is preferable that a plastic film with permeability (breathability) is used, from the viewpoint of preventing sweatiness in the absorbent product 1 and providing comfortable feeling to the wearer. In the present embodiment, a plastic film with permeability whose weight per unit area is equal to or more than $10 \text{ g/m}^2$ and equal to or less than $40 \text{ g/m}^2$ is used as the back sheet 23.

As shown in FIG. 2, the absorbent part 22 has an upper absorbent layer 221 in which an opening 2211 is formed, an absorbent sheet 222 which is located at the lower side of the upper absorbent layer 221 (i.e., between the upper absorbent layer 221 and the back sheet 23) and which covers the opening 2211 at the lower side of the opening 2211, and a lower absorbent layer 223 which is located at the lower side of the absorbent sheet 222 (i.e., between the absorbent sheet 222 and the back sheet 23).

The upper absorbent layer 221 has a fiber assembly layer 2212 in which the above opening 2211 is formed at a position facing (to face) a crotch region of the wearer, and super absorbent materials 2213 which are mixed with the fiber assembly layer 2212 and held thereto. The fiber assembly layer 2212 is formed of, for example regenerated hydrophilic fibers (such as cellulose, rayon, cotton), synthetic fibers, pulp fibers or the like, and super absorbent polymers (SAP (Super Absorbent Polymer)), super absorbent fibers (SAF (Super Absorbent Fiber)), or the like are used as the super absorbent materials 2213. In the present embodiment, fibrillated pulp fibers are stacked so as to become about 100 to $400 \text{ g/m}^2$, to form the fiber assembly layer 2212, and granular absorbent resin such as polyacrylic acid, cellulose, starch-acrylonitrile is used as the super absorbent materials 2213. Preferably, the upper absorbent layer 221 contains the super absorbent materials 2213 where the percentage by weight of the super absorbent materials 2213 in the upper absorbent layer 221 is equal to or more than 10 and equal to or less than 70. In FIG. 2, the super absorbent materials 2213 are enlarged and the number of the super absorbent materials 2213 is less than that in the actual absorbent product 1 for easy understanding of the drawing (the same applies to after-mentioned super absorbent materials 2222, 2232).

As shown in FIG. 1, the upper absorbent layer 221 has an approximately rectangular shape elongated in the longitudinal direction in a planar view, and the opening 2211 has an oval shape elongated in the longitudinal direction. In addition, both side portions of the opening 2211 are overlapped with the pair of side sheets 3. In the present embodiment, a width of the opening 2211 at the approximate middle of the upper absorbent layer 221 in the longitudinal direction is equal to or more than 10% and equal to or less than 50% of a width of the upper absorbent layer 221. As shown in FIG. 2, the upper absorbent layer 221 has a convex part 2214 protruding toward the top sheet 21 and lying along the whole edge of the opening 2211. A height of the convex part 2214 (i.e., protruding thickness) is preferably equal to or more than 10% and equal to or less than 80% of a thickness of the upper absorbent layer 221 at periphery of the convex part 2214.

As shown in FIG. 1, the absorbent sheet 222 has an approximately rectangular shape elongated in the longitudinal direction, and its outer edge almost wholly overlaps with that of the upper absorbent layer 221 in the planar view. As shown in FIG. 2, the absorbent sheet 222 has two liquid-pervious sheets 2221, 2223, and super absorbent materials 2222 located between the stacked sheets 2221, 2223. Preferably, each sheet 2221, 2223 is hydrophilic, and for example, a point-bond nonwoven fabric, air-through nonwoven fabric, spunlace nonwoven fabric or tissue paper is utilized as the sheet 2221, 2223. Similar material to the above super absorbent materials 2213 is used for the super absorbent materials 2222, and the super absorbent materials 2222 are fixed to the sheet 2221 and the sheet 2223 with adhesive (not shown) applied on the sheet 2221 and/or the sheet 2223 in the form of straight lines, curved lines or the like. There may be a case where a plurality of lines of adhesive each of which is short and straight are applied over in the form of fibers in application of adhesive on the sheet 2221 or the sheet 2223.

In the present embodiment, an air-through nonwoven fabric or spunlace nonwoven fabric whose weight per unit area is equal to or more than $10 \text{ g/m}^2$ and equal to or less than $50 \text{ g/m}^2$ is used as the sheet 2221, 2223, and the super absorbent materials 2222 are bonded to the sheets 2221, 2223 with rubber hot melt adhesive applied on any one of the sheets 2221, 2223 where weight per unit area of the hot melt adhesive is equal to or more than $3 \text{ g/m}^2$ and equal to or less than $50 \text{ g/m}^2$. Preferably, weight per unit area of the super absorbent materials 2222 is equal to or more than $100 \text{ g/m}^2$ and equal to or less than $250 \text{ g/m}^2$.

Figure 3:
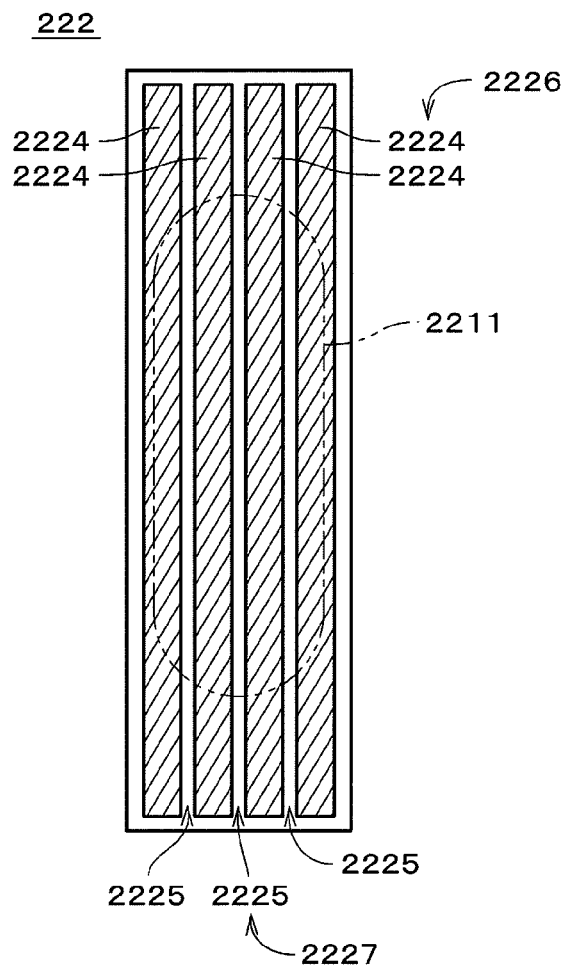
FIG. 3 is a plan view of an absorbent sheet.

FIG. 3 is a plan view showing the absorbent sheet 222. In FIG. 3, hatching lines are drawn at a plurality of areas 2224 (in the present embodiment, four areas) in which the super absorbent materials 2222 (see FIG. 2) are located, and the opening 2211 in the upper absorbent layer 221 is drawn with chain double-dashed lines (the same applies to FIG. 8). As shown in FIG. 3, the plurality of areas 2224 are arranged in the width direction of the absorbent part 22, and each of them is band-like continuously extending in the longitudinal direction of the absorbent part 22. In the following description, the plurality of areas 2224 arranged in stripes are generically referred to as an "absorbent area 2226".

A plurality of areas 2225 lying around the absorbent area 2226 (i.e., each area 2225 lies between two areas 2224 adjacent to each other) are areas 2225 in which the super absorbent materials 2222 do not exist between the two sheets 2221, 2223. Each area 2225 extends continuously and linearly along the longitudinal direction of the absorbent part 22 from a position under the opening 2211 (i.e., the position is included in the opening 2211 in the planar view). In the following description, the plurality of areas 2225 arranged in stripes are generically referred to as a "non-absorbent area 2227". It can be considered that the non-absorbent area 2227 is a low density area in which a density of the super absorbent materials 2222 is lower than that in the surrounding absorbent area 2226. In the absorbent sheet 222, the sheet 2221 and the sheet 2223 shown in FIG. 2 are bonded to each other by heat bonding (thermal fusion bonding) in the non-absorbent area 2227 spreading continuously and linearly along the longitudinal direction of the absorbent part 22, and therefore each of the plurality of areas 2224 in the absorbent area 2226 is apart from the other areas 2224. Thus, the super absorbent materials 2222 located in one area 2224 are prevented from being moved to the other areas 2224.

As shown in FIG. 1, the lower absorbent layer 223 is larger than the upper absorbent layer 221 and the absorbent sheet 222 in the planar view, and a shape of the lower absorbent layer 223 in the planar view is identical to a shape of the above absorbent part 22. As shown in FIG. 2, the lower absorbent layer 223 has a fiber assembly layer 2231 and super absorbent materials 2232 which are mixed with the fiber assembly layer 2231 and held thereto. Preferably, the lower absorbent layer 223 contains the super absorbent materials 2232 where the percentage by weight of the super absorbent materials 2232 in the lower absorbent layer 223 is equal to or more than 10 and equal to or less than 70. In a similar fashion to the fiber assembly layer 2212 of the upper absorbent layer 221 described above, the fiber assembly layer 2231 is formed of, for example regenerated hydrophilic fibers (such as cellulose, rayon, cotton), synthetic fibers, pulp fibers or the like, and in the present embodiment, fibrillated pulp fibers are stacked so as to become about 100 to 400 g/m$^2$, to form the fiber assembly layer 2231. In a similar fashion to the super absorbent materials 2213 of the upper absorbent layer 221, super absorbent polymers, super absorbent fibers or the like are used as the super absorbent materials 2232, and in the present embodiment, granular absorbent resin such as polyacrylic acid, cellulose, starch-acrylonitrile is used.

In the absorbent product 1, an inner side surface of the opening 2211 in the upper absorbent layer 221 and a portion of the absorbent sheet 222 which covers (i.e., closes) the opening 2211 (i.e., the portion which is exposed through the opening 2211) are coated with the top sheet 21, to form a concave part facing the crotch region of the wearer, and excrement such as urine excreted from the wearer comes into the concave part. Through the top sheet 21, moisture of the excrement is led to the portion of the absorbent sheet 222 covering the opening 2211. The moisture is diffused to the peripheral (i.e., diffused in the longitudinal direction and the width direction) by the topside sheet 2221 of the absorbent sheet 222, and it is absorbed by the super absorbent materials 2222 of the absorbent sheet 222 and the upper absorbent layer 221.

Figure 4:
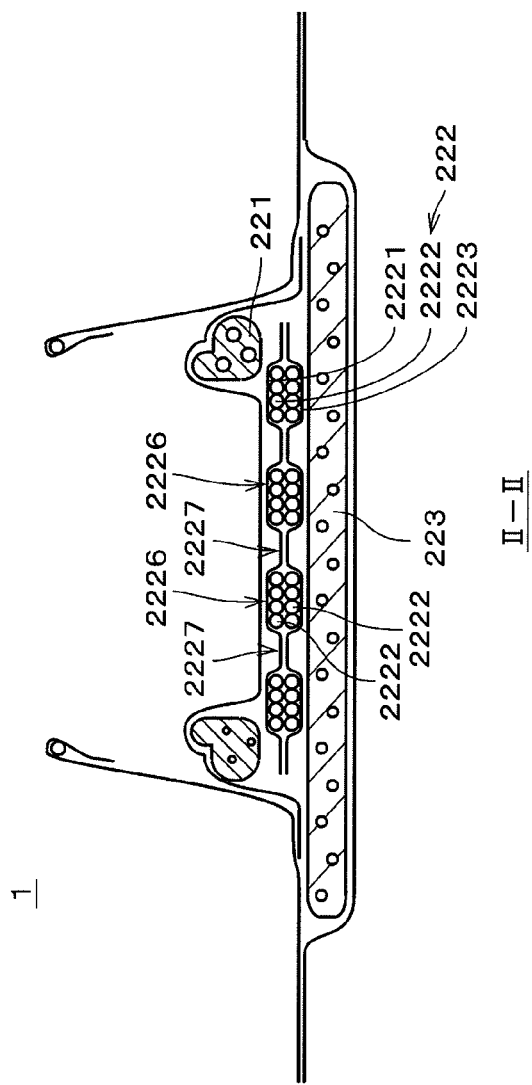
FIG. 4 is a cross-sectional view of the absorbent product.

Since the super absorbent materials 2222 has lower absorption speed and larger absorption capacity than the fiber assembly layer 2212 of the upper absorbent layer 221, some moisture diffused by the sheet 2221 is rapidly absorbed into the upper absorbent layer 221 and subsequently, mainly remaining moisture is absorbed into the absorbent sheet 222 to be held by the super absorbent materials 2222. Some of moisture absorbed by the absorbent sheet 222 is led to the lower absorbent layer 223 through the non-absorbent area 2227 and it is absorbed by the lower absorbent layer 223. The super absorbent materials 2222 which have absorbed moisture swell as shown in FIG. 4. In the absorbent sheet 222, a thickness of the absorbent area 2226 (in FIG. 4, the absorbent area 2226 is denoted by a plurality of reference signs 2226, and the same applies to FIG. 7 described later) increases by swelling of the super absorbent materials 2222, an upper surface of the absorbent area 2226 pushes the upper absorbent layer 221, and a lower surface of the absorbent area 2226 pushes the lower absorbent layer 223.

Figure 5:
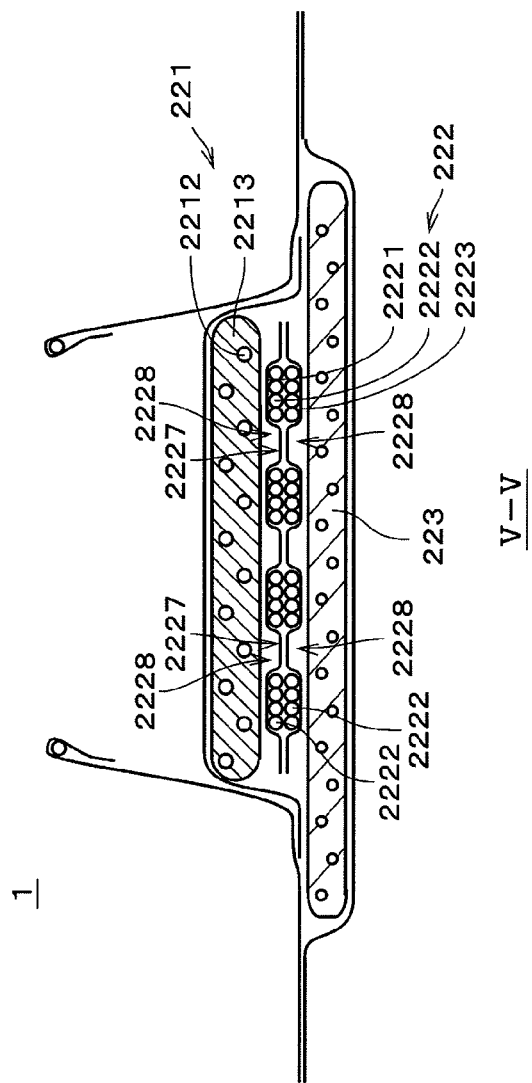
FIG. 5 is a cross-sectional view of the absorbent product.

In the non-absorbent area 2227, since the two sheets 2221, 2223 are bonded to each other, the non-absorbent area 2227 does not swell. FIG. 5 is a cross-sectional view of the absorbent product 1 taken along a line V-V in FIG. 1 where the absorbent product 1 is cross-sectioned with a plane orthogonal to the longitudinal direction. Because of existence of the non-absorbent area 2227, spaces 2228 extending in the longitudinal direction from the opening 2211 (see FIG. 3) are formed between the non-absorbent area 2227 and the upper absorbent layer 221 and between the non-absorbent area 2227 and the lower absorbent layer 223 in the absorbent sheet 222.

In an absorbent product such as an auxiliary absorbent pad or a disposable diaper, multiple excretions (multiple excretion behaviors) are performed by a wearer depending on circumstances. However, in the absorbent product 1 in accordance with the preferred embodiment, after absorption of moisture of excrement in the first excretion, a plurality of spaces 2228 extending in the longitudinal direction from the opening 2211 are formed in the absorbent part 22. Therefore, through the spaces 2228, moisture of excrement in the second excretion and later can be quickly diffused over a wide area along the longitudinal direction of the absorbent part 22 and the moisture of excrement can be absorbed in a wide area of the absorbent part 22. As the result, it is possible to maintain high absorbing ability in multiple excretions in the absorbent product 1 (that is, the absorbent product 1 can have large absorption capacity where moisture in multiple excretions is absorbed enough).

In addition, some of the moisture diffused in the longitudinal direction through the spaces 2228 is rapidly absorbed by the upper absorbent layer 221 which is located on the upside of the spaces 2228 and which has relatively high absorption speed, and subsequently the remaining moisture is absorbed by the super absorbent materials 2222, 2232 which are located on the both left and right sides and the lower side of the spaces 2228 and which have relatively large absorption capacity. Therefore, even if a relatively large amount of excrement such as urine is excreted, moisture of the excrement is prevented from flowing back into the opening 2211 from the spaces 2228 and prevented from coming into contact over a wide area of the skin of the wearer.

In the absorbent part 22, out of the two sheets 2221, 2223 in the absorbent sheet 222, the sheet 2221 located between the upper absorbent layer 221 and the super absorbent materials 2222 is hydrophilic, and therefore moisture of the excrement can be quickly diffused over a wide area between the upper absorbent layer 221 and the absorbent sheet 222. Since the sheet 2223 located between the super absorbent materials 2222 and the lower absorbent layer 223 is also hydrophilic, moisture of the excrement can be quickly diffused over a wide area between the lower absorbent layer 223 and the absorbent sheet 222. In the absorbent sheet 222, because of heat bonding, the sheets 2221, 2223 can be bonded to each other easily and reliably in the non-absorbent area 2227.

In the absorbent part 22, since the upper absorbent layer 221 having the fiber assembly layer 2212 contains super absorbent materials 2213 where the percentage by weight of the super absorbent materials 2213 in the upper absorbent layer 221 is equal to or more than 10, absorption capacity of the upper absorbent layer 221 can be increased without upsizing the upper absorbent layer 221. Since the upper absorbent layer 221 contains super absorbent materials 2213 where the percentage by weight of the super absorbent materials 2213 in the upper absorbent layer 221 is equal to or less than 70, absorption capacity of the upper absorbent layer 221 can be increased while suppressing decrease in absorption speed of the upper absorbent layer 221.

In the absorbent product 1, since the upper absorbent layer 221 comprises the convex part 2214 lying along the edge of the opening 2211 as shown in FIG. 2, it can be suppressed that the excrement excreted into the opening 2211 flows out of the opening 2211 and spreads on the top sheet 21. As the result, the excrement can be prevented from coming into contact over a wide area of the skin of the wearer. In addition, since the lower absorbent layer 223 is provided on the lower side of the absorbent sheet 222 in the absorbent product 1, absorption capacity of the absorbent part 22 can be further increased. Furthermore, since the lower absorbent layer 223 contains the super absorbent materials 2232 where the percentage by weight of the super absorbent materials 2232 in the lower absorbent layer 223 is equal to or more than 10 and equal to or less than 70 in a similar fashion to the upper absorbent layer 221, absorption capacity of the lower absorbent layer 223 can be increased without upsizing the lower absorbent layer 223 while suppressing decrease in absorption speed of the lower absorbent layer 223.

Figure 6:
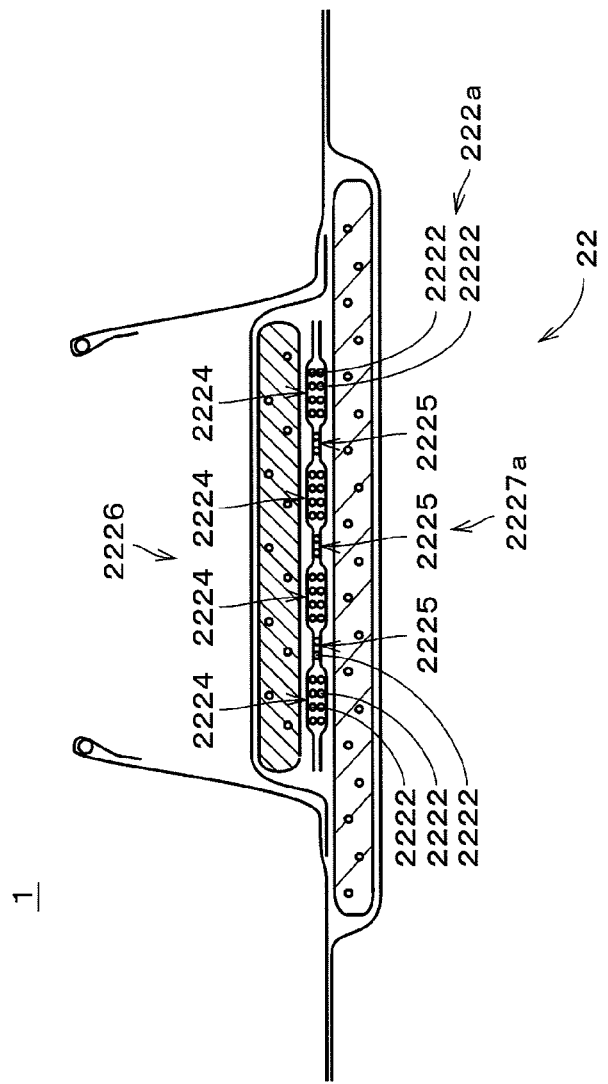
FIG. 6 is a cross-sectional view showing another example of absorbent product.
Figure 7:
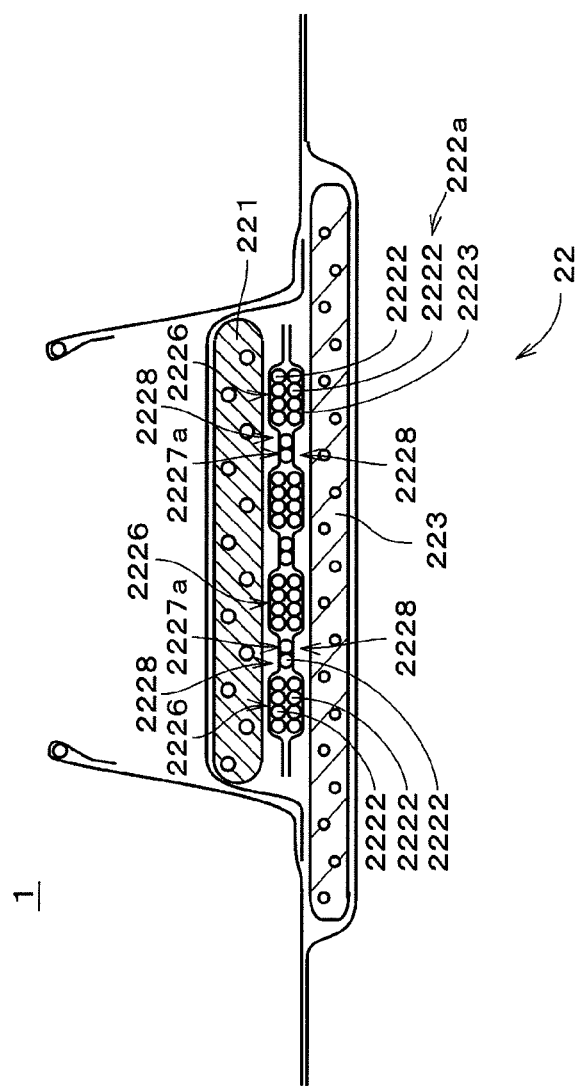
FIG. 7 is a cross-sectional view of the absorbent product.

FIG. 6 is a view showing another example of absorbent sheet and it is a cross-sectional view at a position corresponding to the above FIG. 5. In the absorbent sheet 222a of absorbent product 1 shown in FIG. 6, the super absorbent materials 2222 exist in the plurality of areas 2225 located between the plurality of areas 2224 of the absorbent area 2226. The plurality of areas 2225 are a low density area 2227a in which a density of the super absorbent materials 2222 is lower than that in the peripheral absorbent area 2226 (i.e., the other area of the absorbent sheet 222a). In the absorbent product 1, since the absorbent part 22 absorbs moisture of excrement, the super absorbent materials 2222 in the absorbent sheet 222a swell in the absorbent area 2226 and the low density area 2227a, and the thickness of the absorbent sheet 222a increases as shown in FIG. 7. However, since the thickness of the low density area 2227a is smaller than that of the absorbent area 2226 (i.e., high density area), the plurality of spaces 2228 extending in the longitudinal direction from the opening 2211 (see FIG. 3) are formed between the upper absorbent layer 221 and the low density area 2227a and between the lower absorbent layer 223 and the low density area 2227a. Therefore, through the spaces 2228, moisture of excrement in the second excretion and later can be quickly diffused over a wide area along the longitudinal direction of the absorbent part 22 and the moisture of excrement can be absorbed in a wide area of the absorbent part 22. As the result, it is possible to maintain high absorbing ability in multiple excretions in the absorbent product 1 shown in FIG. 6.

From the viewpoint of diffusing moisture of excrement in the second excretion and later over a wider area more quickly by enlarging the spaces 2228, it is preferable that the two sheets 2221, 2223 are bonded to each other in the plurality of areas 2225 (see FIG. 3).

Next, discussion will be made on an absorbent product in accordance with a second preferred embodiment of the present invention. The absorbent product in accordance with the second preferred embodiment has the same structure as the absorbent product 1 shown in FIGS. 1 to 3 except for a point where the absorbent product has an absorbent sheet 222b shown in FIG. 8 as a substitute for the absorbent sheet 222 shown in FIG. 3. In the following description, out of constituent elements of the absorbent product in accordance with the second preferred embodiment, elements corresponding to respective elements in the absorbent product 1 are denoted by the same reference signs as the respective elements.

Figure 8:
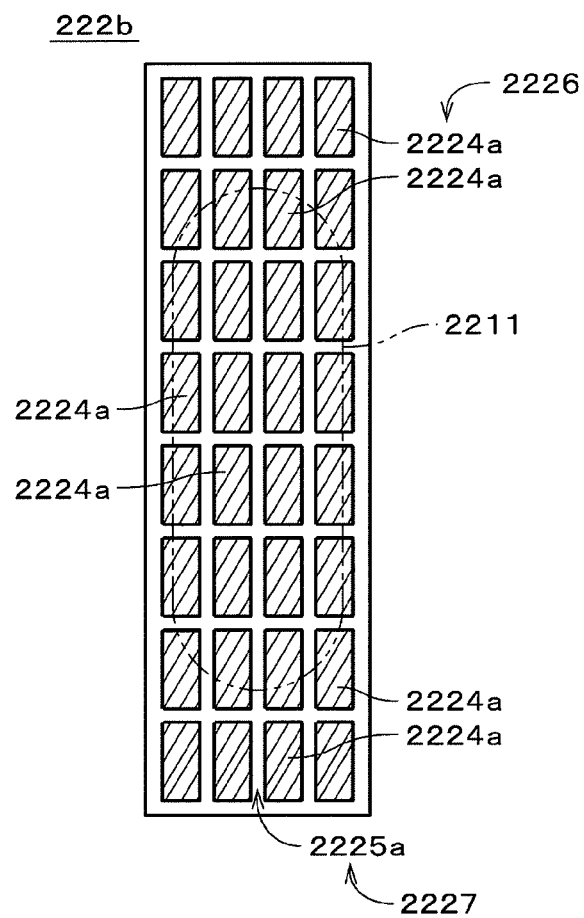
FIG. 8 is a plan view of an absorbent sheet of an absorbent product in accordance with a second preferred embodiment.

As shown in FIG. 8, in the absorbent sheet 222b, a plurality of rectangular areas 2224a arranged in a matrix (i.e., two-dimensionally arranged in the longitudinal direction and the width direction) are the absorbent area 2226 where the super absorbent materials 2222 (see FIG. 2) are located, and a mesh-like area 2225a among the plurality of areas 2224a is the non-absorbent area 2227 where the super absorbent materials 2222 do not exist. It can be considered that the non-absorbent area 2227 is a low density area in which a density of the super absorbent materials 2222 is low as compared to the surrounding area. The non-absorbent area 2227 spreads continuously from positions under the opening 2211 along the longitudinal direction of the absorbent part 22 (see FIG. 1) in the form of mesh, and the two sheets 2221, 2223 (see FIG. 2) of the absorbent sheet 222b are bonded to each other in the non-absorbent area 2227 by heat bonding.

In the absorbent product in accordance with the second preferred embodiment, since the absorbent part 22 absorbs moisture of excrement, the super absorbent materials 2222 in the absorbent sheet 222b swell and the spaces 2228 (see FIG. 5) spreading from the opening 2211 along the longitudinal direction in the form of mesh are formed between the upper absorbent layer 221 (see FIG. 5) and the non-absorbent area 2227 and between the lower absorbent layer 223 (see FIG. 5) and the non-absorbent area 2227 in a similar fashion to the first preferred embodiment. Therefore, through the spaces 2228, moisture of excrement in the second excretion and later can be quickly diffused over a wide area along the longitudinal direction and the width direction of the absorbent part 22, and the moisture of excrement can be absorbed in a wide area of the absorbent part 22. As the result, it is possible to maintain high absorbing ability in multiple excretions in the absorbent product.

In the absorbent product in accordance with the second preferred embodiment, since the excrement led into the spaces 2228 is able to move in the width direction of the absorbent part 22 in addition to the longitudinal direction, the moisture of excrement can be diffused over a wider area more quickly. On the other hand, since the absorbent product 1 in accordance with the first preferred embodiment can hold a relatively large amount of super absorbent materials 2222 between the sheets 2221, 2223 of the absorbent sheet 222, absorption capacity of the absorbent sheet 222 can be increased easily.

Though the preferred embodiments of the present invention have been discussed above, the present invention is not limited to the above-discussed preferred embodiments, but allows various variations.

Figure 9:
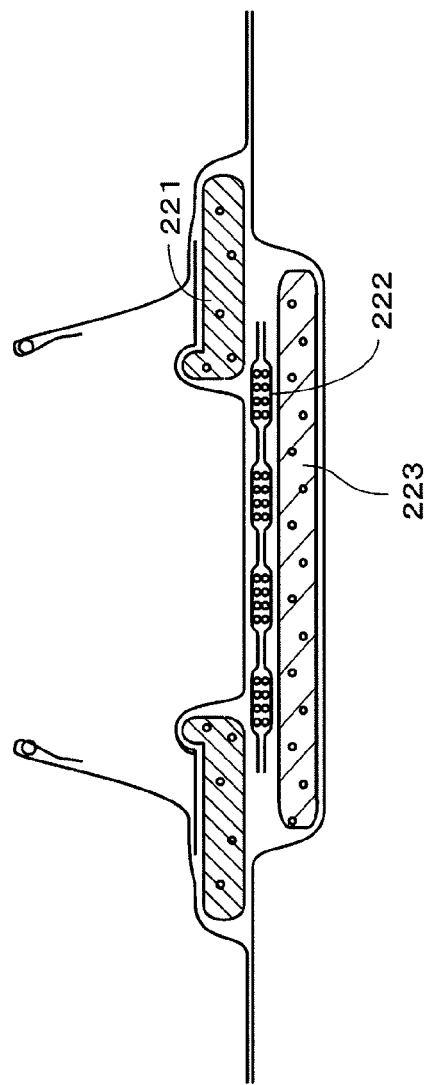
FIG. 9 is a cross-sectional view showing still another example of absorbent product.

For example, as shown in FIG. 9, a width of the upper absorbent layer 221 in the absorbent part 22 (see FIG. 1) may be larger than a width of the absorbent sheet 222 and a width of the lower absorbent layer 223. In the upper absorbent layer 221 shown in FIG. 2, as long as excrement excreted to the inside of the opening 2211 is prevented (or suppressed) from flowing out toward the top sheet 21, the convex part 2214 around the opening 2211 may be omitted.

As described above, the non-absorbent area 2227 having the plurality of linear areas 2225 is provided in the absorbent sheet 222 in accordance with the first preferred embodiment. However, for example, only one linear area 2225 may be provided as the non-absorbent area 2227 in the absorbent sheet 222. In addition, there may be a case where the area 2225 is for example, in the form of a meandering line or in a sawtooth waveform. In the absorbent sheet 222b of the absorbent product in accordance with the second preferred embodiment, the super absorbent materials 2222 whose density is low as compared to the area 2224a may be located in the mesh-like area 2225a.

In the absorbent sheet in accordance with the above preferred embodiments, bonding of the sheets 2221, 2223 in the non-absorbent area 2227 may be performed by for example, ultrasonic bonding or adhesive bonding with hot melt adhesive or the like. The super absorbent materials 2222 are not necessarily fixed to the both sheets 2221, 2223, and they have only to be fixed to at least one of the two sheets 2221, 2223.

In the absorbent part 22, a plurality of openings may be formed at a portion of the upper absorbent layer 221 facing the crotch region of the wearer. In the case where absorption capacity of the absorbent part 22 is enough, the lower absorbent layer 223 may be omitted. In this case, the lower sheet 2223 of the absorbent sheet may be made to be a water-repellent or liquid-impervious sheet. A width of the absorbent part 22 may be almost uniform across the entire length thereof in the longitudinal direction.

Structure of the above absorbent product may be applied to various absorbent products such as a pants-type (i.e., pull-up type) disposable diaper which has a waist opening at an upper end and a pair of leg openings on a lower part, an open-type (tape-type) disposable diaper where a portion located on the front side of a wearer and a portion located on the back side are fastened around the waistline of the wearer in wearing the disposable diaper, an auxiliary absorbent pad for incontinence which is attached at the inside of these disposable diapers and the like to be used, a sanitary napkin, and a panty liner.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 absorbent product
21 top sheet
22 absorbent part
23 back sheet
221 upper absorbent layer
222, 222a, 222b absorbent sheet
223 lower absorbent layer
2211 opening
2212, 2231 fiber assembly layer
2213, 2222 super absorbent material
2214 convex part
2221, 2223 sheet
2227 non-absorbent area
2227a low density area

The invention claimed is:

1. An absorbent product for receiving excrement from a wearer, comprising:
   a liquid-pervious top sheet;
   a water-repellent or liquid-impervious back sheet; and
   an absorbent part located between said top sheet and said back sheet, wherein said absorbent part comprises
      an upper absorbent layer having a fiber assembly layer in which an opening is formed at a position facing a crotch region of a wearer, and
      an absorbent sheet which is located between said upper absorbent layer and said back sheet, said top sheet being coated on said absorbent sheet such that said top sheet together with said absorbent sheet directly covers said opening at the lower side of said opening so as to close said opening,
   wherein said absorbent sheet comprises
      two sheets, and
      super absorbent materials which are located between said two sheets and which are fixed to at least one of said two sheets,
   and wherein a low density area lies between said two sheets and spreads continuously from positions under said opening along a longitudinal direction of said absorbent part in the form of lines or mesh, and a density of said super absorbent materials in said low density area is lower than that in another area of said absorbent sheet or said super absorbent materials do not exist in said low density area.

2. The absorbent product according to claim 1, wherein said super absorbent materials do not exist in said low density area, and said two sheets are bonded to each other in said low density area.

3. The absorbent product according to claim 2, wherein said two sheets are bonded to each other by heat bonding.

4. The absorbent product according to claim 3, wherein said absorbent part further comprises a lower absorbent layer having a fiber assembly layer which is located between said absorbent sheet and said back sheet.

5. The absorbent product according to claim 2, wherein said absorbent part further comprises a lower absorbent layer having a fiber assembly layer which is located between said absorbent sheet and said back sheet.

6. The absorbent product according to claim 1, wherein said low density area is in the form of mesh.

7. The absorbent product according to claim 6, wherein said absorbent part further comprises a lower absorbent layer having a fiber assembly layer which is located between said absorbent sheet and said back sheet.

8. The absorbent product according to claim 1, wherein one of said two sheets which is located between said upper absorbent layer and said super absorbent materials is hydrophilic.

9. The absorbent product according to claim 8, wherein said absorbent part further comprises a lower absorbent layer having a fiber assembly layer which is located between said absorbent sheet and said back sheet.

10. The absorbent product according to claim 1, wherein said upper absorbent layer contains super absorbent materials, the percentage by weight of said super absorbent materials in said upper absorbent layer being equal to or more than 10 and equal to or less than 70.

11. The absorbent product according to claim 10, wherein said absorbent part further comprises a lower absorbent layer having a fiber assembly layer which is located between said absorbent sheet and said back sheet.

12. The absorbent product according to claim 1, wherein said upper absorbent layer comprises a convex part protruding toward said top sheet and lying along an edge of said opening.

13. The absorbent product according to claim 12, wherein said absorbent part further comprises a lower absorbent layer having a fiber assembly layer which is located between said absorbent sheet and said back sheet.

14. The absorbent product according to claim 1, wherein said absorbent part further comprises a lower absorbent layer having a fiber assembly layer which is located between said absorbent sheet and said back sheet.

* * * * *